(12) United States Patent
Dobos et al.

(10) Patent No.: US 8,580,860 B2
(45) Date of Patent: Nov. 12, 2013

(54) FOAMABLE ALCOHOLIC COMPOSITION

(75) Inventors: Kelly Ann Dobos, Akron, OH (US);
Marcia Snyder, Stow, OH (US);
Christine Hall, Omaha, NE (US);
Amanda Jo Copeland, Seville, OH (US)

(73) Assignee: Gojo Industries, Inc., Akron, OH (US)

( * ) Notice: Subject to any disclaimer, the term of this patent is extended or adjusted under 35 U.S.C. 154(b) by 0 days.

(21) Appl. No.: 12/032,083

(22) Filed: Feb. 15, 2008

(65) Prior Publication Data

US 2008/0207767 A1 Aug. 28, 2008

Related U.S. Application Data

(60) Provisional application No. 60/891,243, filed on Feb. 23, 2007, provisional application No. 60/980,194, filed on Oct. 16, 2007.

(51) Int. Cl.
*A01N 31/00* (2006.01)
*A01P 1/00* (2006.01)
*B01F 3/04* (2006.01)

(52) U.S. Cl.
USPC .......................................... 514/724; 516/14

(58) Field of Classification Search
None
See application file for complete search history.

(56) References Cited

U.S. PATENT DOCUMENTS

| | | | |
|---|---|---|---|
| 2,855,367 A | 10/1958 | Buck | 252/138 |
| 4,919,837 A | 4/1990 | Gluck | 252/106 |
| 4,981,678 A | 1/1991 | Tomlinson | 424/45 |
| 5,167,950 A | 12/1992 | Lins | 424/47 |
| 5,629,006 A * | 5/1997 | Hoang et al. | 424/405 |
| 5,776,430 A | 7/1998 | Osborne et al. | 424/43 |
| 5,789,371 A | 8/1998 | Tracy et al. | 510/490 |
| 5,922,663 A | 7/1999 | Gabriel et al. | 510/299 |
| 5,952,290 A | 9/1999 | Li et al. | 510/493 |
| 5,955,416 A | 9/1999 | Baillely et al. | 510/357 |
| 6,277,359 B1 | 8/2001 | Raths et al. | 424/65 |
| 6,339,165 B1 | 1/2002 | Endo et al. | 554/227 |
| 6,358,914 B1 | 3/2002 | Gabriel et al. | 510/528 |
| 6,551,605 B2 | 4/2003 | Bonda | 424/401 |
| 6,664,256 B1 | 12/2003 | Oohkuchi et al. | 514/236.5 |
| 6,664,356 B1 | 12/2003 | Shih | 526/328.5 |
| 6,666,217 B2 | 12/2003 | Elsner et al. | 134/25.2 |
| 6,710,022 B1 | 3/2004 | Kwetkat et al. | 510/119 |
| 6,777,384 B2 | 8/2004 | Raths et al. | 510/475 |
| 6,794,345 B2 | 9/2004 | Elsner et al. | 510/220 |
| 6,797,687 B2 | 9/2004 | Kischkel et al. | 510/475 |
| 6,805,141 B2 | 10/2004 | Elsner et al. | 134/25.2 |
| 6,946,120 B2 | 9/2005 | Wai-Chiu et al. | 424/70.1 |
| 7,141,237 B2 | 11/2006 | Abram et al. | 424/45 |
| 7,164,041 B1 | 1/2007 | Moore et al. | 564/82 |
| 7,393,817 B2 | 7/2008 | Kwetkat et al. | 510/126 |
| 2003/0203824 A1 | 10/2003 | Staats | 510/141 |
| 2004/0033913 A1 | 2/2004 | Dahms et al. | 510/119 |
| 2005/0031653 A1 | 2/2005 | Kwetkat et al. | 424/401 |
| 2005/0063925 A1 | 3/2005 | Candau | |
| 2005/0152931 A1 | 7/2005 | SaNogueira et al. | 424/401 |
| 2006/0194057 A1 | 8/2006 | Pfluecker et al. | 428/404 |
| 2006/0246149 A1 | 11/2006 | Buchholz et al. | 424/603 |
| 2006/0257334 A1 | 11/2006 | Dahms et al. | 424/59 |
| 2006/0275226 A1 | 12/2006 | Dahms et al. | 424/59 |
| 2007/0027055 A1 | 2/2007 | Koivisto et al. | 510/383 |
| 2007/0148101 A1 | 6/2007 | Snyder et al. | 424/47 |
| 2008/0015271 A1 | 1/2008 | Abram et al. | 521/94 |

FOREIGN PATENT DOCUMENTS

| | | |
|---|---|---|
| WO | WO 01/19943 | 3/2001 |
| WO | WO 2006/094387 | 9/2006 |
| WO | 2006138111 | 12/2006 |

OTHER PUBLICATIONS

Woodruff, published in SPC, Feb. 2005.*
Gruber et al., Abstracts of Papers, 234th ACS National Meeting, Boston, MA, United States, Aug. 19-23, 2007, COLL-385.*
Extended European Search Report including European Search Opinion, May 26, 2008.

* cited by examiner

*Primary Examiner* — Bong-Sook Baek
(74) *Attorney, Agent, or Firm* — Renner Kenner Greive Bobak Taylor & Weber

(57) ABSTRACT

A foamable composition includes greater than about 40 weight percent of an alcohol, based upon the total weight of the alcoholic composition, and a foaming surfactant selected from gemini surfactants, sulfuric acid esters, di-esters, $C_{10\text{-}34}$ fatty alcohols, polyquaternium polymers, and combinations thereof.

8 Claims, No Drawings

FOAMABLE ALCOHOLIC COMPOSITION

RELATED APPLICATIONS

This application gains priority from U.S. Provisional Application No. 60/891,243, filed Feb. 23, 2007, and 60/980,194, filed Oct. 16, 2007, both of which are incorporated herein by reference.

TECHNICAL FIELD

This invention relates to foamable alcoholic compositions, and more particularly, to foamable alcoholic compositions that include a foaming surfactant selected from gemini surfactants, sulfuric acid esters, di-esters, $C_{10-34}$ fatty alcohols, polyquaternium polymers, and combinations thereof.

BACKGROUND OF THE INVENTION

Foam cleaning products are popular, in part because they are easier to spread on surfaces. Consumers seem to prefer the luxury of foamed soap products. Less foam is needed to produce the same cleaning power as liquids or gels, due at least partly to the higher surface area of the foam. Properly formulated foam products do not produce the drip and splash that is experienced with traditional gelled or liquid products, because the formulation is not dispensed in a liquid state. This prevents damage to the floors and walls of facilities where the product dispensers are used. Manufacturing of foam products may be easier than gelled products, which often incorporate powdered thickeners that are difficult to handle.

Aqueous foam cleaning products have been described, for example, a foam cleaning composition containing a surfactant, a foam-boosting solvent such as a glycol, and at least 80 percent by weight (wt. %) water.

Alcoholic products are popular as sanitizers for the skin. However, foaming products based upon alcoholic compositions are problematic, because alcohol is known to have strong defoaming properties. Although aerosol-based alcoholic foams are available, these aerosol products are generally more expensive to manufacture than non-aerosol foams.

A skin disinfecting formulation has been described that comprises: (a) an alcohol in an amount from about 50 to about 80 weight percent of the total composition; (b) from about 0.02 wt. % to about 5 wt. % of a block copolymer; (c) from about 5 wt. % to about 25 wt. % of a foaming surfactant; (d) from about 0 wt. % to about 3 wt. % of a thickening agent; (e) from about 1 wt. % to about 5 wt. % of an emulsifier; (f) from about 0 wt. % to about 5 wt. % of a preservative; (g) from about 1 wt. % to about 10 wt. % of a cleaning agent; (h) from about 0.5 wt. % to about 5 wt. % of a polyalkylene glycol; (i) from about 0.05 wt. % to about 5 wt. % of a moisturizer and/or emollient; and (j) from about 6 wt. % to about 30 wt. % of water. The foaming surfactants that are taught are ammonium fatty sulfo succinate, cocamide DEA, alkanolamides such as cocodiethanolamide, amine oxides such as cetyldimethyl amine oxide and amphoterics such as isostearoamphoropionate and lauramidopropyl betaine surfactant.

Commercially available non-aerosol alcoholic foams have been formulated with specific perfluoroalkyl phosphate surfactants and dispensed from a foaming pump mechanism. But the foam thus produced is fleeting, and will immediately begin to deflate or liquefy into a water-thin liquid. Foams have been formulated with silicone surfactants, however these formulations may not be suitable for all applications. Silicone-containing formulations may be very substantive to surfaces, and can interfere with subsequent surface treatment. Thus, there is a need for widely-applicable foamable alcoholic compositions.

SUMMARY OF THE INVENTION

One or more embodiments of this invention provide a foamable composition comprising at least about 40 weight percent alcohol, based upon the total weight of the alcoholic composition; and a foaming surfactant selected from the group consisting of gemini surfactants, sulfuric acid esters, di-esters, $C_{10-34}$ fatty alcohols, polyquaternium polymers, and combinations thereof, with the proviso that where the foaming surfactant comprises an anionic di-ester, the foamable composition further comprises a fatty alcohol or a foam booster.

One or more embodiments of this invention further provide an antimicrobial composition comprising at least about 50 weight percent alcohol, based upon the total weight of the alcoholic composition; from about 0.05 to about 4 wt. % of a surfactant selected from the group consisting of gemini surfactants, sulfuric acid esters, di-esters, $C_{10-34}$ fatty alcohols, polyquaternium polymers, and combinations thereof, and from about 0.005 to about 4 wt. % of a foam booster selected from the group consisting of PVP/VA copolymers, P/VA copolymers, collagen amino acids, soluble elastin, and sodium cocoyl hydrolyzed amaranth protein.

One or more embodiments of this invention still further provide a method for forming alcoholic foam, the method comprising combining an alcohol, a foaming surfactant selected from the group consisting of gemini surfactants, sulfuric acid esters, di-esters, $C_{10-34}$ fatty alcohols, polyquaternium polymers, and combinations thereof, to form a foamable alcoholic composition, with the proviso that where the foaming surfactant comprises an anionic di-ester, the foamable composition further comprises a fatty alcohol or a foam booster; mixing said alcoholic composition and air or an inert gas in a mixing chamber to form a mixture; and passing said mixture through a mesh screen to form a foam, wherein said foamable alcoholic composition comprises at least about 40 percent by weight alcohol, based upon the total weight of the alcoholic composition.

DETAILED DESCRIPTION OF ILLUSTRATIVE EMBODIMENTS

Foamable alcoholic compositions in accordance with this invention include at least one alcohol and at least one foaming surfactant. In one embodiment, the alcohol is a lower alkanol, i.e. an alcohol containing 1 to 4 carbon atoms. Typically, these alcohols have antimicrobial properties. Examples of lower alkanols include, but are not limited to, methanol, ethanol, propanol, isopropanol, butanol, isobutanol, tertiary butanol, and mixtures thereof. In one embodiment, the alcohol comprises ethanol.

Generally, the alcoholic composition comprises an amount of alcohol of at least about 40 weight percent (wt. %), based upon the total weight of the alcoholic composition. In one embodiment, the alcoholic composition comprises at least about 45 weight percent alcohol, in another embodiment, the alcoholic composition comprises at least about 50 weight percent alcohol, and in yet another embodiment, the alcoholic composition comprises at least about 60 weight percent alcohol, based upon the total weight of alcoholic composition. More or less alcohol may be required in certain instances, depending particularly on other ingredients and/or the amounts thereof employed in the composition. In certain embodiments, the alcoholic composition comprises from about 40 weight percent to about 98 weight percent alcohol, in other embodiments, the alcoholic composition comprises from about 45 weight percent to about 95 weight percent of alcohol, in yet other embodiments, the alcoholic composition comprises from about 50 weight percent to about 90 weight percent of alcohol, and in still other embodiments, the alcoholic composition comprises from about 60 weight percent to about 80 weight percent of alcohol, based upon the total weight of the alcoholic composition.

The foamable composition may include a mixture of $C_{1-9}$ alkanols. In one or more embodiments, the foamable composition includes a mixture of one or more $C_{1-4}$ alkanols and one or more $C_{5-9}$ alkanols. The mixture may include primary, secondary, or tertiary alcohols.

The foaming surfactant contributes foaming properties to the alcoholic composition, and may include gemini surfactants (also called dimeric surfactants), sulfuric acid esters, di-esters, fatty alcohols, polyquaternium polymers, or combinations thereof.

In one or more embodiments, the foaming surfactant includes a gemini surfactant. In contrast to simple surfactants, which usually consist of a single hydrophilic head and one or two hydrophobic tails, gemini surfactants have two or more head groups and two or more tails.

In general, a gemini surfactant includes at least two hydrophobic chains, at least two ionic or polar groups, and a spacer. The gemini structure may be symmetrical (i.e. the tails are identical and the heads are identical) or unsymmetrical. In one or more embodiments, the gemini surfactant includes three or four tails.

Examples of polar groups include polyethers and sugars. Examples of ionic groups include positive and negative ions. Specific examples of ionic groups include ammonium, phosphate, sulphate, and carboxylate. In one or more embodiments, the head includes one or more sulphate groups.

Examples of spacers include polar and nonpolar groups. Specific examples of spacer groups include amides, short or long methylene groups, stilbene, polyether, aliphatic, and aromatic groups. In one or more embodiments, the spacer includes a hydrocarbon chain methylene group.

In one or more embodiments, gemini surfactants may be represented by the general schematic

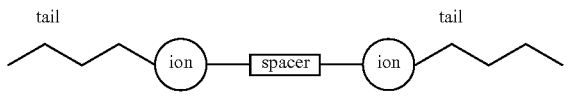

Gemini surfactants may be selected for use in the present invention based upon one or more characteristics, such as tail length, degree of branching, ionic nature of the head group, counterion type, number of heads (i.e. dimer, trimer, tetramer, and the like), spacer solubility (i.e. hydrophobic or hydrophilic), spacer length, and the molecular rigidity of the spacer.

In certain embodiments, the gemini surfactant further includes an ionic or polar group at the unbound end of each tail. These ionic or polar groups may be referred to as terminal ionic or terminal polar groups. Examples of suitable terminal ionic groups include ammonium, phosphate, sulphate, and carboxylate groups.

In one or more embodiments, the gemini surfactant may be represented by the formula

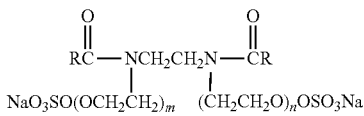

where each R is independently a lipophilic chain, and m and n are independently an integer from 1 to about 500. Examples of lipophilic chains include organic groups having from about 2 to about 26 carbon atoms.

In one embodiment, the gemini surfactant includes disodium ethylene dicocamide PEG-15 disulfate.

In yet another embodiment, the gemini surfactant may be represented by the formula

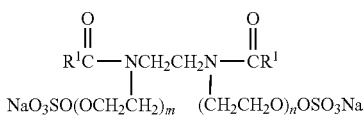

where each $R^1$ independently includes a siloxane group or a fluorinated organic group, and m and n are independently an integer from 1 to about 500. In one or more embodiments, $R^1$ includes $—(Si—O)_xSi(CH_2)_3$ or $—(CF_2)_zCH_3$, where x is an integer from 1 to about 26 and z is an integer from 1 to about 26.

Gemini surfactants are further described in U.S. Pat. No. 6,710,022, which is incorporated herein by reference.

In one or more embodiments, the foaming surfactant includes a sulfuric acid ester. In general, sulfuric acid esters include a sulphate group that may be represented by the formula

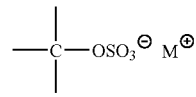

In one embodiment, the sulfuric acid ester includes a sulfuric acid ester of a polyether, glycol, or polyol. In one embodiment, the sulfuric acid ester includes a sulfuric acid ester of a fatty alcohol, and may be prepared by reacting a fatty alcohol with chlorosulfonic acid or sulfur trioxide.

In one or more embodiments, the sulfuric acid ester may be selected for advantageous properties based upon the fatty alcohol chain length. In one embodiment, the foaming surfactant includes a salt of a sulfuric acid ester with sodium, diethanolamine, triethanolamine, or ammonia.

Examples include dimethicone PEG-7 sulfate, sodium PEG-4 cocamide sulfate, sodium PEG-4 lauramide sulfate, sodium cocomonoglyceride sulfate, sodium stearoyl chondroitin sulfate, sodium lauryl sulfate, sulfated glyceryl oleate, and combinations thereof. In one embodiment, the foaming surfactant includes sodium lauryl sulfate.

In one or more embodiments, the foaming surfactant includes a diester, i.e. contains two or more ester groups. In certain embodiments, the foaming surfactant includes a long chain fatty acid di-ester. In one embodiment, the diester is an anionic diester.

Examples of anionic diesters include, sodium stearoyl lactylate, sodium behenoyl lactylate, sodium oleoyl lactylate, sodium cocoyl lactylate, sodium caproyl lactylate, lauroyl lactylic acid, myristoyl lactylic acid, or combinations thereof.

Additional examples include triethanolamine salts, diethanolamine salts, potassium salts, calcium salts, or ammonium salts of stearoyl lactylate, behenoyl lactylate, oleoyl lactylate, cocoyl lactylate, caproyl lactylate, lauroyl lactylic acid, myristoyl lactylic acid, or combinations thereof.

In one or more embodiments, where the foaming surfactant includes an anionic diester, the foamable composition contains less than about 0.1 wt. % of a fluorosurfactant or siloxane surfactant, based upon the total weight of the foamable composition. In other embodiments, where the foaming surfactant includes an anionic diester, the foamable composition contains less than about 0.01 wt. % of a fluorosurfactant or siloxane surfactant. In yet other embodiments, where the foaming surfactant includes an anionic diester, the foamable composition contains less than about 0.005 wt. % of a fluorosurfactant or siloxane surfactant. In certain embodiments, where the foaming surfactant includes an anionic diester, the foamable composition is devoid of a fluorosurfactant or siloxane surfactant.

In one or more embodiments, where the foaming surfactant includes an anionic di-ester, the foamable composition further includes a fatty alcohol as described hereinbelow. In certain embodiments where the foaming surfactant includes an anionic di-ester, the foamable composition further includes one or more foam boosters as described hereinbelow.

In one or more embodiments, a fatty alcohol may be employed to contribute foaming properties to the alcoholic composition. In one or more embodiments, the fatty alcohol contains from about 10 to about 34 carbon atoms. The fatty alcohol may be linear or branched, saturated or unsaturated. Combinations of two or more fatty alcohols may be employed. Examples of fatty alcohols include, but are not limited to, capric alcohol, lauric alcohol, auroleic alcohol, myristic alcohol, myristoleic alcohol, palmitic alcohol, pamitoleic alcohol, stearic alcohol, oleic alcohol, linoleic alcohol, linolenic alcohol, arachidic alcohol, gadoleic alcohol, behenic alcohol, erucic alcohol, clupanodinic alcohol, lignoceric alcohol, cerotic alcohol, montanic alcohol, myricic alcohol, lacceroic alcohol, and geddic alcohol.

In one or more embodiments, the fatty alcohol contains from about 12 to about 28 carbon atoms, and in other embodiments, from about 12 to about 22 carbon atoms. In one embodiment, the fatty alcohol includes lauric, myristic, palmitic, stearic, or behenic alcohol, or a combination thereof. Lauric alcohol is sometimes referred to as n-dodecanol, 1-dodecanol, dedecyl alcohol, or lauryl alcohol. Myristic alcohol is sometimes referred to as 1-tetradecanol or myristyl alcohol. Palmitic alcohol is sometimes referred to as 1-hexadecanol, cetyl alcohol, or palmityl alcohol. Stearic alcohol is sometimes referred to as 1-octadecanol, octadecyl alcohol, or stearyl alcohol. Behenic alcohol is sometimes referred to as 1-docosanol or behenyl alcohol.

The amount of foaming surfactant is not particularly limited, so long as an effective amount to produce foaming is present. In certain embodiments, the effective amount to produce foaming may vary, depending upon the amount of alcohol and other ingredients that are present. In one or more embodiments, the alcoholic composition includes at least about 0.05 wt. % of foaming surfactant, based upon the total weight of the alcoholic composition. In another embodiment, the alcoholic composition includes at least about 0.06 wt. % of foaming surfactant, based upon the total weight of the alcoholic composition. In yet another embodiment, the alcoholic composition includes at least about 0.07 wt. % of foaming surfactant, based upon the total weight of the alcoholic composition.

In one embodiment, the foaming surfactant is present in an amount of from about 0.05 to about 40 weight percent, based upon the total weight of the alcoholic composition. In another embodiment, the foaming surfactant is present in an amount of from about 0.1 to about 30 weight percent, in other embodiments, from about 0.5 to about 10 weight percent, and in yet other embodiments, from about 1 to about 5 weight percent, based upon the total weight of the alcoholic composition. It is envisioned that higher amounts may also be effective to produce foam. All such weights as they pertain to listed ingredients are based on the active level and therefore do not include carriers or by-products that may be included in commercially available materials, unless otherwise specified.

In certain embodiments, the effective amount of fatty alcohol to produce foaming is at least about 0.001 weight percent of fatty alcohol, based upon the total weight of the alcoholic composition. In another embodiment, the alcoholic composition includes at least about 0.005 weight percent of fatty alcohol, based upon the total weight of the alcoholic composition. In yet another embodiment, the alcoholic composition includes at least about 0.01 weight percent of fatty alcohol, based upon the total weight of the alcoholic composition. In still another embodiment, the alcoholic composition includes at least about 0.02 weight percent of fatty alcohol, based upon the total weight of the alcoholic composition.

In one embodiment, the fatty alcohol is present in an amount of from about 0.001 to about 10 weight percent, and in another embodiment, from about 0.002 to about 5 weight percent, based upon the total weight of the alcoholic composition. In another embodiment, the fatty alcohol is present in an amount of from about 0.01 to about 4 weight percent, based upon the total weight of the alcoholic composition. It is envisioned that higher amounts may also be effective to produce foam.

In certain embodiments where the foaming alcoholic composition of the present invention includes a cleansing or sanitizing product that is applied to a surface and then rinsed off, higher amounts of foaming surfactant may be employed. In these embodiments, the amount of foaming surfactant is present in amounts up to about 40 wt. %, based upon the total weight of the composition.

In certain embodiments, advantageous results are achieved when the foamable composition includes a combination of two or more foaming surfactants. In one embodiment, the foamable composition includes a fatty alcohol as described herein and an anionic di-ester. In another embodiment, the foamable composition includes a gemini surfactant and a sulfuric acid ester. In yet another embodiment, the foamable composition includes a gemini surfactant, a sulfuric acid ester, and an anionic di-ester. In one or more embodiments, the foamable composition includes a gemini surfactant and a di-ester. In one embodiment, the amount of gemini surfactant relative to the di-ester is from about 0.6:1 to about 1.7:1 on a weight percent basis.

In one or more embodiments, the foaming surfactant is added directly to the alcoholic composition. In other embodiments, the foaming surfactant is added to the alcoholic composition as a solution or emulsion. In other words, the foaming surfactant may be premixed with a carrier to form a foaming surfactant solution or emulsion, with the proviso that the carrier does not deleteriously affect the foaming properties of the alcoholic composition. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the foaming surfactant is premixed to form a foaming surfactant solution or emulsion, the amount of solution or emulsion that is added to the alcoholic composition may be selected so that the amount of foaming surfactant falls within the ranges set forth hereinabove.

Foaming surfactant mixtures, solutions or emulsions are commercially available, for example under the trade names Ceralution®, from Sasol, Biobase from Tri-K Industries, Inc., and Ritamulse and Ritafactant from RITA Corporation.

In certain embodiments, the alcoholic composition of the present invention further includes at least one foam booster.

In one embodiment, the foam booster may be selected from polymeric or oligomeric foam boosters. In another embodiment, the foam booster may be polymeric or non-polymeric. In one embodiment, the foam booster comprises a cationic oligomer or polymer.

Polymeric foam boosters include polyquaternium polymers. In general, a polyquaternium polymer is one that is designated as such by the CTFA. Polyquaternium polymers may be characterized by containing a quaternary ammonium group. Non-limiting examples of polyquaterniums include those listed in Table 1, below, including the INCI name and technical name.

TABLE 1

| INCI Name Polyquaternium-X | Technical Name |
|---|---|
| -2 | Bis(2-chloroethyl)ether, polym. w. N,N'-bis[3-(dimethylamino)propyl]urea |
| -4 | Hydroxyethylcellulose Dimethyldiallylammoinum Chloride Copolymer |
| -5 | Copolymer of acrylamide and beta-methacrylyloxyethyl trimethyl ammonium methosulfate |
| -6 | Polydimethyldiallyl Ammonium Chloride |
| -7 | Dimethyldiallyl Ammonium Chloride & Acrylamide Copolymer |
| -9 | Polydimethyaminoethyl methacrylate quaternized with Methyl Bromide |
| -10 | Hydroxyethylcellulose reacted with trimethyl ammonium substituted epoxide |
| -11 | PVP N,N-Dimethyl Aminoethyl Methacrylic Acid Copolymer Diethyl Sulfate Soln |
| -14 | Ethanaminium, N,N,N-Trimethyl-2-[(2-methyl-1-oxo-2-propenyl)oxy]-, Methyl Sulfate Homopolymer |
| -15 | Acrylamide-Dimethylaminoethyl Methacrylate Methyl Chloride Copolymer |
| -16 | 3-Methyl-1-Vinylimidazolium Chloride-1-Vinyl-2-Pyrrolidinone Chloride |
| -17 | Quat salt made from Adipic acid & diethylaminopropylamine & dichloroether |
| -18 | Quat salt prepared by the reaction of adipic acid and dimethylaminopropylamine, reacted with dichloroethyl ether |
| -19 | Quat ammonium salt prepared by the reaction of polyvinyl alcohol with 2,3-epoxypropylamine |
| -20 | Quat ammonium salt prepared by the reaction of polyvinyl octadecyl ether with 2,3-epoxypropylamine |
| -22 | Acrylic Acid-Diallyldimethylammonium Chloride (DADMAC) Polymer |
| -22 | Acrylic Acid-Diallyldimethylammonium Chloride (DADMAC) Polymer |
| -24 | Polyquat ammonium salt of hydroxyethyl cellulose reacted with lauryl dimethyl ammonium substituted epoxide |
| -27 | Block Copolymer of Polyquaternium-2 and 17 |
| -28 | Vinylpyrrolidone/Methacrylamidopropyltrimethylammonium Chloride Copolymer |
| -29 | Propoxylated Chitosan quaternized with epichlorhydrin |
| -30 | Ethanaminium, N-Carboxymethyl)-N,N-Dimethyl-2-((2-Methyl-1-Oxo-2-Propenyl)Oxy)-, Inner Salt, Polymer with Methyl 2-Methyl-2-Propenoate |
| -31 | 2-propane nitrile reaction product w/N,N-dimethylpropanediamine, Sulfate |
| -32 | Acrylamide-Dimethylaminoethyl Methacrylate Methyl Chloride (DMAEMA) Copolymer |
| -37 | Trimethylaminoethyl Methacrylate Chloride Polymer |
| -39 | Acrylic Acid (AA), Polymer w/ Acrylamide & Diallyldimethylammonium Chloride(DADMAC) |
| -42 | Polyoxyethylene (dimethyliminio)ethylene-(dimethyliminio)ethylene dichloride |
| -43 | Copolymer of Acrylamide, acrylamidopropyltrimonium chloride, amidopropylacrylamide & DMAPA Monomers |
| -44 | Polyquat ammonium salt of vinylpyrrilidone & quaternized imidazoline monomers |
| -46 | Quat ammonium salt of vinylcaprolactum, vinylpyrrolidone &methylvinylimidazolium |
| -47 | Quat ammonium chloride-acrylic acid, methyl acrylate & methacrylamidopropyltrimonium Chloride |
| -48 | Copolymer of methacryolyl ethyl betaine, 2-hydroxyethylmethacrylate & methacryloylethyltrimethylammonium chloride |
| -51 | 3,5,8-Triox-4-Phosphaundec-10-en-1-aminium, 4-Hydroxy-N,N,N,10-Tetramethyl-9-Oxo, Inner Salt, 4-Oxide, Polymer with Butyl 2-Methyl-2-Propenoate |
| -53 | Acrylic Acid (AA)/Acrylamide/Methacrylamidopropyltrimonium Chloride (MAPTAC) Copolymer |
| -54 | Polymeric quaternary ammonium salt prepared by the reaction of aspartic acid and C6-18 alkylamine with dimethylaminopropylamine and sodium chloroacetate |
| -55 | 1-Dodecanaminium, N,N-Dimethyl-N-[3-[(2-Methyl-1-Oxo-2-Propenyl)AminoPropyl]-, Chloride, Polymer with N-[3-(Dimethylamino)Propyl]-2-Methyl-2-Propenamide and 1-Ethenyl-2-Pyrrolidinone |
| -56 | Polymeric quaternary ammonium salt prepared by the reaction of aspartic acid and C6-18 alkylamine with dimethylaminopropylamine and sodium chloroacetate. |

TABLE 1-continued

| INCI Name Polyquaternium-X | Technical Name |
|---|---|
| -57 | Polymeric quaternary ammonium salt consisting of Castor Isostearate Succinate (q.v.) and Ricinoleamidopropyltrimonium Chloride (q.v.) monomers |
| -58 | 2-Propenoic Acid, Methyl Ester, Polymer with 2,2-Bis[(2-Propenyloxy)Methyl]-1-Butanol and Diethenylbenzene, Reaction Products with N,N-Dimethyl-1,3-Propanediamine, Chloromethane-Quaternized |
| -59 | Polyquaternium polyester |
| -60 | 9-Octadecenoic Acid, 12-Hydroxy-, [(2-Hydroxyethyl)Imino]Di-2,1-Ethanediyl Ester, Polymer with 5-Isocyanato-1-(Isocyanatomethyl)-1,3,3-Trimethylcyclohexane, Compd. with Diethyl Sulfate |
| -62 | Polymeric quaternary ammonium salt prepared by the reaction of butyl methacrylate, polyethylene glycol methyl ether methacrylate, ethylene glycol dimethacrylate and 2-methacryloyethyl trimonium chloride with 2,2'-azobis(2-methyl propionamidine) dihydrochloride |
| -63 | Copolymer of acrylamide, acrylic acid and ethyltrimonium chloride acrylate |
| -65 | Polymeric quaternary ammonium salt consisting of 2-methacryloyl-oxyethylphosphorylcholine, butyl methacrylate and sodium methacrylate monomers |
| -68 | Quaternized copolymers of vinylpyrrolidone (VP), methacrylamide (MAM) vinylimidazole(VI) & quaternized vinylimidazole (QVI) |
| -69 | Polymeric quaternary ammonium salt containing vinyl caprolactam, vinylpyrrolidone, dimethylaminopropyl methacrylamide (DMAPA), and methoacryloylaminopropyl lauryldimonium chloride |
| -70 | Polymeric quaternary ammonium salt consisting of an ethoxylated, propoxylated stearyl amine condensed with adipic acid and dilinoleic acid and quaternized with dimethyl sulfate |
| -71 | Poly(hydroxypropyl tetra(2-hydroxypropyl)ethylenediammonium) chlorides |
| -72 | Polymeric quaternary ammonium salt of hydroxethylcellulose reacted with a coco-alkyl dimethyl ammonium substituted epoxide |
| -73 | Polymeric quaternary ammonium salt consisting of propyltrimonium chloride acrylamide, ethyltrimonium chloride methacrylate and dimethylacrylamide monomers |
| -74 | Polymeric quaternary ammonium salt consisting of dimethylamino-propyl methacrylamide, acrylic acid |
| -75 | Polymeric quaternary ammonium salt of Starch Hydroxypropyl-trimonium Chloride (q.v.) and starch hydroxypropylaurdimonium chloride |

In one or more embodiments, the polyquaternium polymer includes a quaternized copolymer of vinylpyrrolidone and dimethylamino methacrylate, a hydrophobically modified quaternized copolymer of vinylpyrrolidone & dimethylaminopropyl methacrylamide, or a mixture thereof.

In one embodiment, the polyquaternium polymer has a molecular weight of from 1,000 to 5,000,000, in another embodiment, from about 1500 to about 2,500,000 and in yet another embodiment, from about 1,000,000 to about 2,000,000.

In one or more embodiments, the polyquaternium polymer may impart foamability to the alcoholic composition in the absence of other foaming surfactant. That is, in one or more embodiments, the polyquaternium polymer may act as a foaming surfactant or as a foam booster. In other embodiments, the polyquaternium polymer may be used in combination with one or more other foaming surfactants. In these or other embodiments, the polyquaternium polymer may include polyquaternium-11, polyquaternium-37, or combinations thereof.

In one or more embodiments where the polyquaternium polymer operates as a foaming surfactant, the polyquaternium polymer may be present in an amount of from about 0.1 to about 5 weight percent active, based upon the total weight of the alcoholic composition. In another embodiment, the polyquaternium polymer is present in an amount of from about 0.4 to about 4.5 weight percent, based upon the total weight of the alcoholic composition, and in yet another embodiment, the polyquaternium polymer is present in an amount of from about 0.5 to about 4 weight percent, based upon the total weight of the alcoholic composition. In other embodiments where the polyquaternium polymer operates as a foam booster, the polyquaternium polymer may be present in an amount suitable for foam booster, as described hereinbelow.

Other foam boosters that may operate to improve foam quality and/or stability include terpolymers of vinylcaprolactam (VCL), vinylpyrrolidone (VP) and dialkylaminoalkyl acrylate, including a VP/vinylcaprolactam/dimethylaminopropyl methacrylamide copolymer. Yet another foam booster includes isobutylene/dimethylaminopropyl maleimide/ethoxylated maleimide/maleic acid copolymer. These and other foam boosters are sometimes referred to as film-forming polymers.

Still other foam boosters include acrylamide/ammonium acrylate copolymer, acrylamides/DMAPA acrylates/methoxy PEG methacrylate copolymer, acrylamide/sodium acryloyldimethyltaurate/acrylic acid copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates copolymer, acrylates/$C_{1-2}$ succinates/hydroxyacrylates copolymer, acrylates/ethylamine oxide methacrylate copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/polytrimethyl siloxymethacrylate copolymer, acrylates/stearyl acrylate/ethylamine oxide methacrylate copolymer, acrylates/trifluoropropylmethacrylate/polytrimethyl siloxymethacrylate copolymer, acrylates/VA copolymer, acrylates/VP copolymer, adipic acid/diethylenetriamine copolymer, adipic acid/ dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium VA/acrylates copolymer, amodimethicone/silsesquioxane copolymer, AMPD-acrylates/diacetoneacrylamide copolymer, AMP-acrylates/allyl methacrylate copolymer, AMP-acrylates/$C_{1-18}$ alkyl acrylates/$C_{1-8}$ alkyl acrylamide copolymer, AMP-acrylates/diacetoneacrylamide copolymer, AMP-acrylates/dimethylaminoethylmethacrylate copolymer, bacillus/rice bran extract/soybean extract ferment filtrate, behenyl methacrylate/ethylamine oxide methacrylate copolymer, bis-butyloxyamodimethicone/PEG-60 copolymer, bis-isobutyl PEG-14/amodimethicone copolymer, bis-isobutyl PEG-15/amodimethicone copolymer, butyl acrylate/ethylhexyl methacrylate copolymer, butyl acrylate/hydroxypropyl dimethicone acrylate copolymer, butyl ester of ethylene/MA copolymer, butyl ester of PVM/MA copolymer, calcium/sodium PVM/MA copolymer, chitosan, chitosan lactate, corn starch/acrylamide/sodium acrylate copolymer, dehydroxanthan gum, diethylene glycolamine/epichlorohydrin/piperazine copolymer, dimethicone crosspolymer, dimethicone/silsesquioxane copolymer, diphenyl amodimethicone, ethyl ester of PVM/MA copolymer, ethyltrimonium chloride methacrylate/hydroxyethylacrylamide copolymer, hydrolyzed wheat protein/PVP crosspolymer, hydroxypropyl dimethiconylpropyl acrylates copolymer, hydroxypropyltrimonium hydrolyzed corn starch, isobutylene/ethylmaleimide/hydroxyethylmaleimide copolymer, isobutylene/MA copolymer, isobutylmethacrylate/trifluoroethylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, lauryl PEG-9 polydimethylsiloxyethyl dimethicone, methacrylic acid/sodium acrylamidomethyl propane sulfonate copolymer, methacryloyl ethyl betaine/acrylates copolymer, methoxy amodimethicone/silsesquioxane copolymer, methoxy PEG-114/polyepsilon caprolactone, myristic/palmitic/stearic/ricinoleic/eicosanedioic glycerides, octylacrylamide/acrylates/butylaminoethyl methacrylate copolymer, PEG-800/polyvinyl alcohol copolymer, PEG/PPG-25/25 dimethicone/acrylates copolymer, PEG-8/SMDI copolymer, polyacrylamide, polyacrylate-6, polyacrylate-8, polyacrylate-9, polyacrylate-15, polyacrylate-16, polyacrylate-17, polyacrylate-18, polyacrylate-19, polybeta-alanine/glutaric acid crosspolymer, polybutylene terephthalate, polyester-1, polyethylacrylate, polyethylene terephthalate, polyimide-1, polymethacryloyl ethyl betaine, polypentaerythrityl terephthalate, polyperfluoroperhydrophenanthrene, polyquaternium-4/hydroxypropyl starch copolymer, polyurethane-1, polyurethane-6, polyurethane-10, polyurethane-18, polyurethane-19, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PVM/MA copolymer, PVP/VA/itaconic acid copolymer, PVP/VA/vinyl propionate copolymer, rhizobian gum, rosin acrylate, shellac, silicone quaternium-16/glycidoxy dimethicone crosspolymer, sodium butyl ester of PVM/MA copolymer, sodium ethyl ester of PVM/MA copolymer, sodium polyacrylate, sodium polygamma-glutamate, soy protein phthalate, sterculia urens gum, terephthalic acid/Isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinylneodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/methacrylamide/vinyl imidazole copolymer, VP/VA copolymer, VP/vinyl caprolactam/DMAPA acrylates copolymer, yeast palmitate, a silicon-based polymer or resin such as phenylpropyldimethyl siloxysilicate, trimethylsiloxysilicate, cyclopentasiloxane, trimethylsiloxysilicate, diisostearoyl trimethyllolpropane siloxy silicate, vinyl dimethicone crosspolymer/blends, and alkyl cetearyl dimethicone crosspolymers.

In one embodiment, the foam booster includes a VP/vinylcaprolactam/dimethylaminopropyl methacrylamide copolymer sold under the trade names Aquaflex SF-40, or an isobutylene/dimethylaminopropyl maleimide/ethoxylated maleimide/maleic acid copolymer sold under the trade name Aquaflex XL-30. In one or more embodiments, the foam booster further includes PVP/VA-630 from ISP (P/VA Copolymer), Collamino 25 from Arch Personal Care (collagen amino acids), Solu-Mar Elastin from Arch Personal Care (soluble elastin), or Amaranth S from Arch Personal Care (sodium cocoyl hydrolyzed amaranth protein).

Advantageous foam boosters also include PVP/VA copolymers, such as PCP/VA-630 from ISP, P/VA copolymers, collagen amino acids such as Collamino 25 from Arch Personal Care, soluble elastin such as Solu-Mar Elastin from Arch Personal Care, and sodium cocoyl hydrolyzed amaranth protein such as Amaranth S from Arch Personal Care.

In one embodiment, foam booster is present in an amount of from about 0.005 to about 4 weight percent active, based upon the total weight of the alcoholic composition. In another embodiment, the foam booster is present in an amount of from about 0.01 to about 1 weight percent, based upon the total weight of the alcoholic composition, and in yet another embodiment, the foam booster is present in an amount of from about 0.02 to about 0.2 weight percent, based upon the total weight of the alcoholic composition.

In one embodiment, the foam booster is added directly to the alcoholic composition. In one or more other embodiments, the foam booster is added to the alcoholic composition as a solution or emulsion. In other words, the foam booster may be premixed with a carrier to form a foam booster solution or emulsion, with the proviso that the carrier does not deleteriously affect the foaming properties of the alcoholic composition. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the foam booster is premixed to form a foam booster solution or emulsion, the amount of solution or emulsion that is added to the alcoholic composition is selected so that the amount of foam booster falls within the ranges set forth hereinabove.

In one embodiment, the weight ratio of foaming surfactant to foam booster is from about 3.5:1 to about 14.5:1, and in another embodiment, the weight ratio of foaming surfactant to foam booster is from about 8:1 to about 11:1.

In certain embodiments, the foam booster increases the foam density and provides a creamier foam. The foam booster may operate to improve the foam in any number of ways. In one or more embodiments, the foam booster also improves the foam quality, i.e. increases the number of bubbles and/or reduces the size of the bubbles.

The alcoholic composition of this invention may further include a wide range of optional ingredients, with the proviso that they do not deleteriously affect the foam forming properties of the alcoholic composition, or the stability of the foam. The CTFA International Cosmetic Ingredient Dictionary and Handbook, Eleventh Edition, 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Non-limiting examples of functional classes of ingredients are described in these references. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, and keratolytics, and the like. In one embodiment, the alcoholic composition further comprises glycerin.

Auxiliary surfactants may be included in the alcoholic compositions for the purpose of boosting or modifying the foam quality and characteristics, for modifying the feel of the final formulation during rub in and/or dry time, for providing persistence or long-lasting microbial action of the alcohol, for solubilizing other ingredients such as fragrances or sunscreens, and for irritation mitigation. Auxiliary surfactants include, but are not necessarily limited to, sulfosuccinates, amine oxides, PEG-80 sorbitan laurate, polyglucosides, alkanolamides, sorbitan derivatives, fatty alcohol ethoxylates, quaternary ammonium compounds, amidoamines, sultaines, isothionates, sarcosinates, betaines, polysorbates and fatty alcohol polyethylene glycols.

Examples of polysorbates include polysorbate-20, which may be referred to as polyoxyethylene sorbitan monolaurate; polysorbate-40, which may be referred to as polyoxyethylene sorbitan monopalmitate; polysorbate-60, which may be referred to as polyoxyethylene sorbitan monostearate; and polysorbate-80, which may be referred to as polyoxyethylene sorbitan monooleate. Additional examples of polysorbates includes polysorbate-21, polysorbate-61, polysorbate-65, polysorbate-81, and polysorbate-85.

The amount of auxiliary agent is not particularly limited, so long as it does not deleteriously affect the foam forming properties of the alcoholic composition, or the stability of the foam. In certain embodiments, one or more auxiliary agents may be present in the foamable alcoholic composition in an amount of from about 0 to about 2 weight percent, based upon the total weight of the alcoholic composition. In other embodiments, one or more auxiliary agents may be present in the foamable alcoholic composition in an amount of from about 0.1 to about 1 weight percent, based upon the total weight of the alcoholic composition and fatty alcohol polyethylene glycols.

In one or more embodiments, the composition of the present invention does not include any foaming surfactants except for those selected from the group consisting of gemini surfactants, sulfuric acid ester surfactants, anionic di-ester surfactants, polyquaternium polymers, and fatty alcohols. In other embodiments, the composition of the present invention may include one or more auxiliary foaming surfactants. Auxiliary foaming surfactants include fluorosurfactants and siloxane polymer surfactants. Fluorosurfactants and siloxane polymer foaming surfactants are described in U.S. patent application Ser. No. 11/438,664, which is hereby incorporated by reference.

Although a propellant may be used to produce stable foam, advantageously a propellant is not necessary. In certain embodiments, the amount of propellant is less than about 1000 parts per million by weight, based upon the total weight of the alcoholic composition. In one embodiment, the alcoholic composition is substantially free of propellants, such as hydrocarbon propellants. By substantially free is meant that the amount of propellant in the alcoholic composition is less than about 100 parts per million by weight, based upon the total weight of the alcoholic composition.

In one embodiment, alcohol is the only active antimicrobial ingredient introduced into the composition, and in this embodiment the amount of auxiliary antimicrobial ingredients is less than about 0.1 weight percent, based upon the total weight of the alcoholic composition. In other embodiments, the composition includes auxiliary antimicrobial agents in addition to alcohol. Examples of auxiliary antimicrobial agents include, but are not limited to, triclosan, also known as 5-chloro-2(2,4-dichlorophenoxy)phenol and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecanediimidi amide; 2-bromo-2-nitropropane-1; 3-diol, benzalkonium chloride; cetylpyridinium chloride; alkylbenzyldimethylammonium chlorides; iodine; phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; benzethonium chloride; methylbenzethonium chloride; and mixtures thereof. When used, the auxiliary antimicrobial agents are present in amounts of from about 0.1 to about 1 wt. %, based upon the total weight of the alcoholic composition.

The alcoholic composition of the present invention may optionally further comprise a wide range of topical drug actives, with the proviso that they do not deleteriously affect the foam forming properties of the alcoholic composition, or the stability of the foam. Examples of topical drug actives include salicylic acid, acetyl salicylic acid, cis-retinoic acid, trans-retinoic acid, N-acetyl-L-cysteine, lipoic acid, azelaic acid, phytic acid, lisophosphotidic acid, tetracycline, ibuprofen, naproxen, acetominophen, hydrocortisone, resorcinol, phenoxyethanol, phenoxypropanol, phenoxyisopropanol, 2,4,4'-trichloro-2'-hydroxy diphenyl ether, 3,4,4'-trichlorocarbanilide, octopirox, 2-phenylbenzimidazole-5-sulfonic acid, dihydroxyacetone, benzoyl peroxide, 2,4,4'-trichloro-2-hydroxy diphenyl ether, phenoxyethanol, phenoxypropanol, phenoxyisopropanol, phytic acid, lipoic acid, lisophosphatidic acid, benoxaprofen, flubiprofen, fenoprofen, fenbufen, ketoprofen, indoprofen, priprofen, carprofen, oxaprozin, pranoprofen, miroprofen, tioxaprofen, suprofen, alminoprofen, tiaprofenic acid, fluprofen, bucloxic acid, benzocaine, lidocaine, bupivacaine, chloroprocaine, dibucaine, etidocaine, mepivacaine, tetracaine, dyclonine, hexylcaine, procaine, cocaine, ketamine, pramoxine, phenol, dihydroxyacetone, tyrosine, ethyltryosinate, phospho-DOPA, .beta.-lactim drugs, quinoline drugs, ciprofloxacin, norfloxacin, erythromycin, amikacin, doxycycline, capreomycin, chlorhexidine, chlortetracycline, oxytetracycline, clindamycin, ethambutol, hexamidinee isethionate, metronidazole, pentamidine, gentamicin, kanamycin, lineomycin, methacyclin, methenamine, minocycine, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxyclcyline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amnanfadine sulfate, octopirox, parachlorometa xylenol, nystatin, tolnaftate, clotrimazole, 2-ethylhexyl p-methoxycinnamate, octyl methoxycinnamate, p-amino benzoate, p-aminobenzoic acid, 2-phenyl benzimidazole-5-sulfonic acid, octocrylene, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, silica, iron oxide, 4-N,N-(2-ethylhexyl)methyl aminobenzoic acid ester of 2,4-dihydroxybenzophenone, 4-N,N-(2-ethylhexyl)methyl aminobenzoic acid ester with 4-hydroxydibenzoylmethane, 4-N,N-(2-ethylhexyl)methyl aminobenzoic acid ester of 2-hydroxy-4-(2-hydroxyethoxy) benzophenone, 4-N,N-(2-ethylhexyl)-methyl aminobenzoic acid ester of 4-(2-hydroxyethoxy)dibenzoylmethane, tetracycline, ibuprofen, naproxen, acetaminophen, resorcinol, 3,4,4'-trichlorocarbanilide, octopirox, pharmaceutically-acceptable salts and mixtures of the above.

In one or more embodiments, the balance of the alcoholic composition includes water or other suitable solvent. In many embodiments of the present invention, the alcoholic composition evaporates after use, and so it is not necessary to rinse or dry after using the composition. These embodiments may be referred to as leave-on or rinse-free compositions. In one embodiment, one or more volatile silicone-based materials are included in the formulation to further aid the evaporation process. Exemplary volatile silicones have a lower heat of evaporation than alcohol. In certain embodiments, use of silicone-based materials can lower the surface tension of the fluid composition. This provides greater contact with the surface. In one embodiment, the silicone-based material, such as cyclomethicone, trimethylsiloxy silicate or a combination thereof, may be included in the formulation at a concentration of from about 4 wt. % to about 50 wt. % and in another embodiment from about 5 wt. % to about 35 wt. %, and in yet another embodiment from about 11 wt. % to about 25 wt. %, based upon the total weight of the alcoholic composition.

In certain embodiments, such as a rinse-off formulation, the balance of the alcoholic composition includes foaming surfactant.

The alcoholic composition may be prepared by simply mixing the components together. The order of addition is not particularly limited. In one embodiment, the skin sanitizing alcoholic composition is prepared by a method comprising dispersing foaming surfactant in alcohol with slow to moderate agitation, adding water, and then adding a foam booster, and mixing until the mixture is homogeneous.

The foamable composition of the present invention may be employed in any type of dispenser typically used for foam products. Advantageously, while the foamable composition can optionally be foamed by aerosolizing the composition, an aerosolized product is not necessary for foaming. Any dispenser that is capable of mixing the foamable alcoholic composition with air or an inert gas may be used. Inert gases include gas that does not substantially react or otherwise deleteriously affect the foamable composition. Examples of inert gases include nitrogen, argon, xenon, krypton, helium, neon, and radon. In one embodiment, the alcoholic composition is used in dispensers that employ foaming pumps, which combine ambient air or an inert gas and the alcoholic composition in a mixing chamber and pass the mixture through a mesh screen. In this and other embodiments, the viscosity of the composition is less than about 100 mPas, in one embodiment less than about 50 mPas, and in another embodiment less than about 25 mPas.

In order to demonstrate the practice of the present invention, the following examples have been prepared and tested. The examples should not, however, be viewed as limiting the scope of the invention. The claims will serve to define the invention.

EXAMPLES

Foamable formulations were prepared by mixing ingredients in the amounts shown in the following tables I to VI. The amounts given are in weight percent.

TABLE 1

| Ingredient | Example 1 | Example 2 |
|---|---|---|
| Ethanol (SDA3C) | 60.00 | 60.00 |
| Proprietary aqueous mixture of 15-25% Disodium Ethylene Dicocamide PEG-15 Disulfate and 15-25% Sodium Lauroyl Lactylate | 0.08 | 0.20 |
| Polyquaternium-11 (20% in water) |  | 0.18 |
| Water | qs 100 | qs 100 |

TABLE II

| Ingredient | Example 3 | Example 4 |
|---|---|---|
| Ethanol (SDA3C) | 60.00 | 60.00 |
| Proprietary aqueous mixture of 15-25% Disodium Ethylene Dicocamide PEG-15 Disulfate and 15-25% Sodium Lauroyl Lactylate | 0.08 | 0.60 |
| Water | 39.92 | 39.40 |

TABLE III

| Ingredient | Example 5 | Example 6 | Example 7 | Example 8 |
|---|---|---|---|---|
| Ethanol (SDA3C) | 60.00 | 60.18 | 60.18 | 60.00 |
| Proprietary aqueous mixture of 15-25% Disodium Ethylene Dicocamide PEG-15 Disulfate and 15-25% Sodium Lauroyl Lactylate* | 0.75 | 0.75 | 0.75 | 0.75 |
| Polyquaternium-11 (20% in water) | 0.1 | | | |
| Isobutylene/Ethylmaleimide/Hydroxyethylmaleimide Copolymer | | 0.25 | | |
| PVM/MA Copolymer | | | 0.06 | |
| Collagen amino acids (25% in water) | | | | 1.00 |
| Water | 39.15 | 38.82 | 39.01 | 38.25 |

TABLE IV

| Ingredient | Example 9 | Example 10 |
|---|---|---|
| Ethanol (SDA3C) | 59.00 | 60.00 |
| Sodium lauroyl lactylate | 1.00 | 1.00 |
| Polyquaternium-11 (20% in water) | | 0.06 |
| Water | 40.00 | 38.94 |

TABLE V

| | Example 11 | Example 12 | Example 13 | Example 14 | Example 15 |
|---|---|---|---|---|---|
| Ethanol (SDA3C) | 60 | 64.50 | 60.00 | 59.35 | 61.32 |
| Proprietary aqueous mixture of 25-45% Sodium lauroyl lactylate, 10-25% Sodium cocoyl Isethionate, and 5-10% Sodium lauroyl glutamate | | 1.20 | | | |
| Sodium alkyl naphthalene sulfonate | | | | 2 | |
| Glyceryl dilaurate | | | | | 0.71 |
| Proprietary aqueous mixture of 85-90% Decyl glucoside, and 10-15% Sodium lauroyl lactylate | | | 1.00 | | |
| Proprietary aqueous mixture of 10-15% Stearyl alcohol and 50-60% Sodium Behenoyl lactylate | 1 | | | | |
| Sodium lauroyl lactylate | | | | 0.65 | 0.68 |
| PEG-150 Pentaerythrityl Tetrastearate[1] | 0.4 | 0.4 | 0.4 | 0.4 | 0.4 |
| Cetyl alcohol | 0.14 | 0.14 | 0.14 | 0.13 | 0.14 |
| Water | qs 100 | qs 100 | qs 100 | qs 100 | qs 100 |

[1] Crothix

TABLE VI

| | Example 16 | Example 17 | Example 18 | Example 19 | Example 20 | Example 21 | Example 22 |
|---|---|---|---|---|---|---|---|
| Ethanol (SDA3C) | 59.82 | 59.82 | 59.82 | 59.82 | 65.0 | 70.0 | 70.0 |
| PEG-150 Pentaerythrityl Tetrastearate | 0.15 | 0.15 | 0.15 | 0.15 | | 0.40 | 0.50 |
| Cetyl alcohol | 0.03 | 0.03 | 0.03 | 0.03 | | 0.14 | |
| VP/VA Copolymer | | 0.1 | | | | | |
| Isobutylene/Ethylmaleimide/Hydroxyethyl-maleimide Copolymer (40% in water) | | | | 0.25 | | | |
| PVM/MA Copolymer | | | | 0.53 | | | 0.53 |
| Polyquaternium-11 (20% in water) | | | | | 0.08 | 2.50 | 2.75 |
| Proprietary aqueous mixture of 39-49% Polyquaternium-37 and 1% 1,3-Butanediol[2] | | | | | 5.00 | 3.50 | 4.75 |
| Water | qs 100 | qs 100 | qs 100 | qs 100 | qs 100 | qs 100 | qs 100 |

[2] Syntran PC5320

The formulations were foamed by using an Airspray foaming pump. Descriptions of the foam are summarized in Table VII. Examples 2 and 4-9 are described relative to Examples 1 and 3. Example 10 is described relative to Example 9. Example 13 is described relative to Examples 11 and 12. Examples 17-19 are described relative to Example 16.

TABLE VII

| Example No. | Description of Foam |
|---|---|
| Example 1 | Slight amount of foam, flat, fleeting |
| Example 2 | Increased level of foam, not as flat, puffier |
| Example 3 | Slight amount of foam, flat, fleeting |
| Example 4 | Whiter foam with lighter bubbles, somewhat flat, lasts longer |
| Example 5 | Whiter foam with tighter bubbles, somewhat flat, lasts longer |
| Example 6 | Whiter form, puffier but still fleeting |
| Example 7 | Whiter foam, puffier but still fleeting |
| Example 8 | Fluffier foam, not as fleeting, lighter bubbles |
| Example 9 | Whiter foam with light bubbles |
| Example 10 | Fluffier foam with light bubbles |
| Example 11 | White and fluffy, collapses quickly |
| Example 12 | White and poufy, collapses quickly |
| Example 13 | White and fluffy, doesn't collapse as quickly, best volume |
| Example 14 | White and fluffy, lasts longer than all others |
| Example 15 | White and poufy, tight bubbles |
| Example 16 | Flat, fleeting foam |
| Example 17 | Foam improved did not collapse as quickly |
| Example 18 | Slightly puffier foam |
| Example 19 | Still flat but did not collapse as quickly |
| Example 20 | White, small amount of volume |
| Example 21 | White, good flash foam |
| Example 22 | White, good volume, best of Examples 20-22 |

Various modifications and alterations that do not depart from the scope and spirit of this invention will become apparent to those skilled in the art. This invention is not to be duly limited to the illustrative embodiments set forth herein.

What is claimed is:

1. A foamable composition comprising:
   at least 60 weight percent of a $C_{1-4}$ alcohol;
   from about 0.1 to about 20 weight percent of a gemini surfactant; and
   from about 0.1 to about 20 weight percent of a di-ester surfactant, wherein all weight percentages are based upon the total weight of the composition,
   wherein said gemini surfactant is disodium ethylene dicocamide PEG-15 disulfate,
   wherein said di-ester surfactant is selected from sodium sodium stearoyl lactylate, sodium behenoyl lactylate, sodium oleoyl lactylate, sodium cocoyl lactylate, sodium caproyl lactylate, lauroyl lactylic acid, myristoyl lactylic acid, triethanolamine stearoyl lactylate, triethanolamine behenoyl lactylate, triethanolamine oleoyl lactylate, triethanolamine cocoyl lactylate, triethanolamine caproyl lactylate, diethanolamine stearoyl lactylate, diethanolamine behenoyl lactylate, diethanolamine oleoyl lactylate, diethanolamine cocoyl lactylate, diethanolamine caproyl lactylate, potassium stearoyl lactylate, potassium behenoyl lactylate, potassium oleoyl lactylate, potassium cocoyl lactylate, potassium caproyl lactylate, calcium stearoyl lactylate, calcium behenoyl lactylate, calcium oleoyl lactylate, calcium cocoyl lactylate, calcium caproyl lactylate, ammonium sodium stearoyl lactylate, ammonium behenoyl lactylate, ammonium oleoyl lactylate, ammonium cocoyl lactylate, ammonium caproyl lactylate or combinations thereof, and
   wherein said foamable composition produces a foam when passed through a non-aerosol foam dispenser.

2. The composition of claim 1, wherein the amount of gemini surfactant relative to the di-ester is from about 0.6:1 to about 1.7:1 on a weight percent basis.

3. The composition of claim 1, wherein said composition further comprises at least one foam booster.

4. The composition of claim 3, wherein said foam booster is a cationic oligomer or polymer, a collagen amino acid, an amaranth protein, or a soluble elastin.

5. The composition of claim 3, wherein the weight ratio of the gemini surfactant to foam booster is from about 3.5:1 to about 14.5:1.

6. An antimicrobial composition comprising:
   at least 60 weight percent of a $C_{1-4}$ alcohol;
   from about 0.1 to about 20 weight percent of a gemini surfactant;
   from about 0.1 to about 20 weight percent of a di-ester surfactant; and
   from about 0.005 to about 4 weight percent of an amaranth protein, wherein all weight percentages are based upon the total weight of the composition,
   wherein said gemini surfactant is disodium ethylene dicocamide PEG-15 disulfate,
   wherein said di-ester surfactant is selected from sodium sodium stearoyl lactylate, sodium behenoyl lactylate, sodium oleoyl lactylate, sodium cocoyl lactylate, sodium caproyl lactylate, lauroyl lactylic acid, myristoyl lactylic acid, triethanolamine stearoyl lactylate, triethanolamine behenoyl lactylate, triethanolamine oleoyl lactylate, triethanolamine cocoyl lactylate, triethanolamine caproyl lactylate, diethanolamine stearoyl lactylate, diethanolamine behenoyl lactylate, diethanolamine oleoyl lactylate, diethanolamine cocoyl lactylate, diethanolamine caproyl lactylate, potassium stearoyl lactylate, potassium behenoyl lactylate, potassium oleoyl lactylate, potassium cocoyl lactylate, potassium caproyl lactylate, calcium stearoyl lactylate, calcium behenoyl lactylate, calcium oleoyl lactylate, calcium cocoyl lactylate, calcium caproyl lactylate, ammonium sodium stearoyl lactylate, ammonium behenoyl lactylate, ammonium oleoyl lactylate, ammonium cocoyl lactylate, ammonium caproyl lactylate or combinations thereof, and
   wherein said foamable composition produces a foam when passed through a non-aerosol foam dispenser.

7. The composition of claim 1, wherein the composition further comprises one or more ingredients selected from emulsifiers, viscosity increasing agents, and detergents, wherein the total amount of emulsifiers, viscosity increasing agents, and detergents is from 0.1 to 1 wt. % based upon the total weight of the alcoholic composition.

8. The composition of claim 1, wherein the composition further comprises auxiliary surfactant in an amount of from 0 to about 2 wt. % based upon the total weight of the alcoholic composition.

* * * * *